United States Patent [19]

Lipson

[11] Patent Number: 5,837,900

[45] Date of Patent: Nov. 17, 1998

[54] SYSTEM AND METHOD FOR DETECTING METAL ION OXIDATION IN PACING LEAD

[75] Inventor: David Lipson, Shoreview, Minn.

[73] Assignee: Medtronic Inc, Minneapolis, Minn.

[21] Appl. No.: 670,793

[22] Filed: Jun. 21, 1996

[51] Int. Cl.$^6$ .......................... G01H 11/06; A61N 1/00; A61N 1/362

[52] U.S. Cl. .................. 73/661; 607/27; 607/28; 607/119

[58] Field of Search ............... 73/662, 649, 658, 73/659, 661, 584; 607/9, 27, 28, 37, 116, 119, 122, 125, 126, 121; 128/642, 734, 661.04, 662.05

[56] References Cited

U.S. PATENT DOCUMENTS

| | | | |
|---|---|---|---|
| 4,899,750 | 2/1990 | Ekwall | 128/419 PG |
| 4,919,145 | 4/1990 | Marriott | 128/723 |
| 5,003,975 | 4/1991 | Hafelfiner et al. | 128/419 PG |
| 5,201,865 | 4/1993 | Kuehn | 128/419 PT |
| 5,343,865 | 9/1994 | Gardineer et al. | 128/662.05 |
| 5,375,609 | 12/1994 | Molacek et al. | 607/119 |
| 5,421,336 | 6/1995 | DeBernardis | 128/662.05 |
| 5,423,881 | 6/1995 | Breyen et al. | 607/122 |
| 5,514,171 | 5/1996 | Hoegnelid et al. | 607/122 |
| 5,534,018 | 7/1996 | Wahlstrand et al. | 607/27 |

*Primary Examiner*—Hezron E. Williams
*Assistant Examiner*—Rose M. Finley
*Attorney, Agent, or Firm*—Harold Patton; Michael Jaro

[57] ABSTRACT

There is provided a system and method for determining the existence of metal ion oxidation degradation in an implanted pacing lead. A micro-vibration driver, preferably operating at a sonic frequency matched to an ultrasound detector, is used to vibrate the proximal end of a stylet that has been inserted into the lumen of a bipolar lead. The shaking of the stylet causes flexural waves to be propagated along the stylet, which in turn flex the lead inner conductor and the insulation between the inner and outer conductor. If metal ion oxidation is present in the insulation, the shaking causes generation of a noise signal which is detectable across the conductors along with the electrogram. The presence of such a noise signal is correlated with the output of the driver, i.e., with the vibration of the lead, to indicate when MIO degradation is present. An ultrasound imaging detector can be used to determine the location of the MIO degradation along the length of the lead.

16 Claims, 2 Drawing Sheets

ON
OFF

SYSTEM AND METHOD FOR DETECTING METAL ION OXIDATION IN PACING LEAD

BACKGROUND OF THE INVENTION

This invention relates to systems and methods for checking the integrity of implanted pacing leads and, more particularly, for determining the presence of metal ion oxidation in pacing leads.

Metal ion oxidation (MIO) has been found to be a problem in implanted bipolar pacing leads. Such bipolar leads have two conductors running the length of the lead, each connecting the proximal end to an electrode at the distal end. The lead conductors are provided as coils, namely an outer coil and an inner coil. An insulation material, polyurethane, is positioned between the two conductors to maintain their electrical integrity, i.e., to prevent shorting of the leads. However, metal ion oxidation can cause degradation of the inner and outer insulative sheaths with time, leading in extreme cases to lead failure. It is very important to detect such insulative failures as soon as possible, and preferably when they are incipient and have not yet adversely affected lead performance. Such a lead failure could cause false sensing and/or loss of bipolar capability, a particularly unsatisfactory circumstance for a patient with an implanted pacemaker system.

There thus exists a need in the art for a reliable method of checking to determine whether a lead has degraded due to MIO. For a patient with an implanted pacing system, the scheduled replacement of a pacemaker presents an opportunity to check the lead. The present method is to take impedance tests, but such tests are insensitive in determining when there is a degree of degradation short of substantial insulation breakdown. What is needed is a test which can detect the start of metal ion oxidation in the inner insulative sheath, so that lead replacement can be more efficaciously prescribed and undertaken.

The present invention is based upon the observation that lead motion seems to be a critical factor which causes oversensing in cases of MIO degradation. It is observed that under such circumstances lead motion induces noise which originates in the area of MIO degradation. Proceeding from this, the invention proposes a test for MIO which involves subjecting the lead to micro-motion and examining the detected signal to see whether there is a correlation between the lead motion and the signal across the lead conductors. Using this principle, there is provided a system and method for detecting a measure of MIO degradation in a pacer lead, and in particular for carrying out such detection on an implanted bipolar lead at time of pacemaker replacement.

SUMMARY OF THE INVENTION

There is provided a system and method for detecting metal ion oxidation in a pacing lead, particularly applicable to an implanted bipolar pacing lead. A stylet is inserted into the exposed proximal end of the lead, and pushed through the lumen formed by the inner conductor. An exposed portion of the proximal end of the lead is attached to a micro-vibrator which are coupled, which is programmable to generate timed sequences of vibrations to the stylet. As the stylet is vibrated and advanced into the lead toward the distal end, an electrogram is sensed between the two conductors of the lead, and examined for noise content. The electrogram is processed to determine when noise is detected which correlates with the vibratory signal which has been coupled to the stylet, whereby a determination is made as to whether or not there is MIO degradation in the lead. The system may also employ ultrasound imaging of the stylet to aid in locating the suspected area of degradation.

DESCRIPTION OF THE PREFERRED EMBODIMENTS

Figure 1:
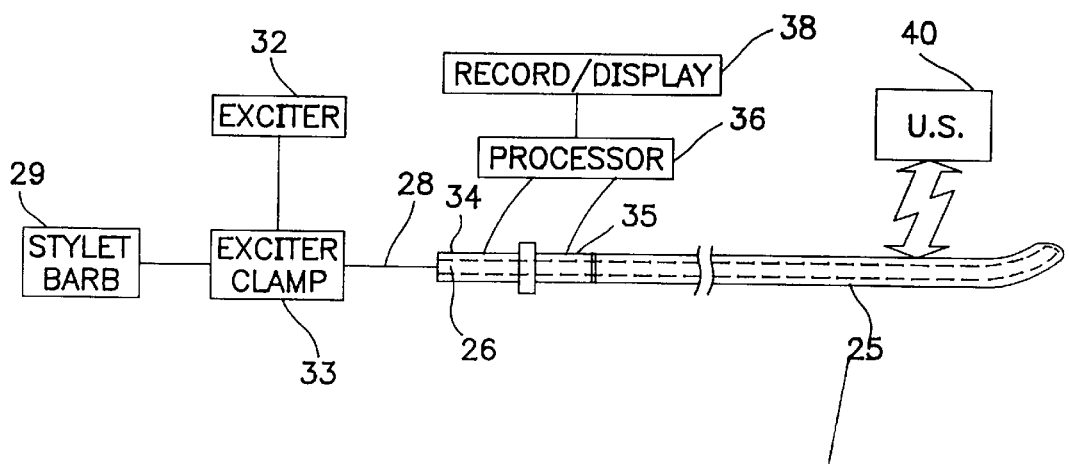
FIG. 1 is a block diagram of the system of this invention for detecting pacemaker lead degradation due to MIO, illustrating the use of a stylet and a micro-vibrator.
Figure 2:
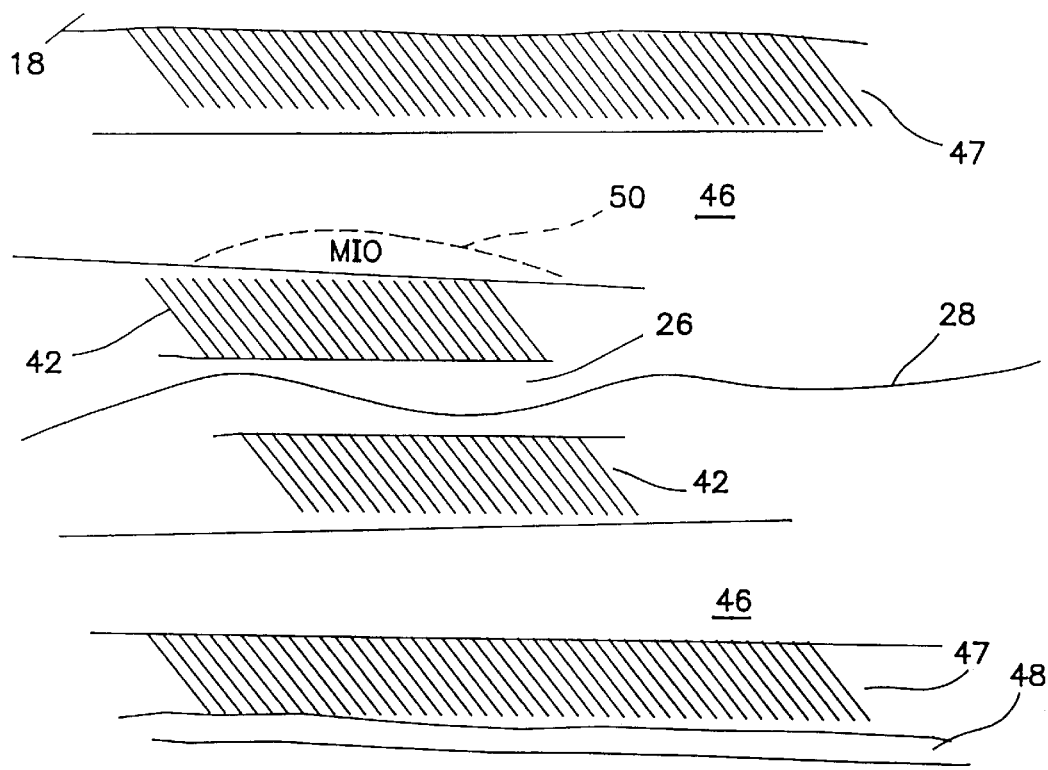
FIG. 2 is an illustrative diagram of a cross section of a bipolar pacing lead, where the lead has a stylet inserted into its lumen and a flexural vibration wave is propagated along the stylet.

Referring now to FIGS. 1 and 2, there are illustrated the primary components of the system of this invention. A pacing lead 25 is shown, having a lumen 26 formed by its inner conductor, or coil 42. In the practice of this invention, the proximal end of the lead is exposed, as at the time of pacemaker replacement. A stylet 28 is inserted into the lumen 26, which stylet can be manipulated by the knob 29 in a know fashion. An exciter 32 has its output connected to exciter clamp 33, which couples the micro-vibrations to the stylet at the position of the exciter on the exposed proximal portion of the stylet. Exciter 32 is suitably a ColorMark Driver, Model CM01DRVR.1, and the clamp 33 is a ColorMark Clip, Model CM011625.1 which includes both the clamp and a cable assembly for connecting to the driver; both are made by EchoCath, Inc. The exciter uses piezoelectric technology to induce flexural waves into the stylet, resulting in propagation of sonic frequency waves having micron-sized amplitudes down the length of the stylet. The driver can be both amplitude and frequency controlled. An ultrasound detector, shown at 40, is suitably a B-scan medical color-flow imaging ultrasound system, for providing a visualization of the stylet, and particularly the stylet tip. The vibration of the stylet is perceived by the doppler receiving portion of unit 40 as motion, which is displayed in color, aiding in locating the MIO degradation.

Electrical signals induced in the two conductors of the lead are picked up at the connector pin 34 and ring 35 respectively, and connected to electronic processor 36. Processor 36 provides the standard functions of amplification and any necessary or desired filtering, and delivers the electrogram signals from the lead to record/display device 38. As can be seen by reference to FIG. 3, when there is MIO degradation, there is detected noise that is sensed concurrently with the micro-vibration, and thus provides an indication of the underlying MIO problem. If noise is detected which does not correlate with the activation of the sonic vibrations, it does not indicate an MIO problem; it may indicate other types of lead failure such as crush, poor joints, etc.

Referring to FIG. 2, there is presented a diagrammatic representation of a longitudinal cross-section of a bipolar pacing lead, having a stylet 28 inserted through the lumen 26, and wherein the stylet is being subjected to sonic vibrations at an exposed proximal portion. The inner coil 42 has around it an inner insulation zone 46, with the outer coil 47 being around the outside of the inner insulation zone. An outer sheath 48 of suitable biocompatible material provides the outer coating of the lead. As illustrated, a flexural wave is transmitted along the stylet, which in turn causes micro shaking of the inner conductor and the inner insulation portion. When a developing MIO zone is present, as illustrated at 50, the shaking or movement of this zone results in noise which correlates with the output from the driver 32. Since the flexural wave represents a periodic propagation of the stylet displacement, every period of the stylet will go through a node and anti-node. Because there is damping of the wave as it propagates, the amplitude slowly decreases toward the distal end of the pacing lead. Although the most common failure zone is 3–6 cm from the distal electrode, MIO can occur in almost any location. Severe MIO near the implanted generator is just as serious as if it is near the heart. Consequently, the entire stylet probes for faults, but the distal segment of the stylet will cause identification of the most proximal degraded region of polymer first, as the stylet is advanced into the lead lumen. Deeper insertion of the stylet may detect additional MIO zones.

Figure 3:
FIG. 3 shows coordinated plots of the vibration signal coupled to the inserted stylet and the resulting electrogram, illustrating noise in the sensed signal which corresponds to a period of stylet vibration.
Figure 3:
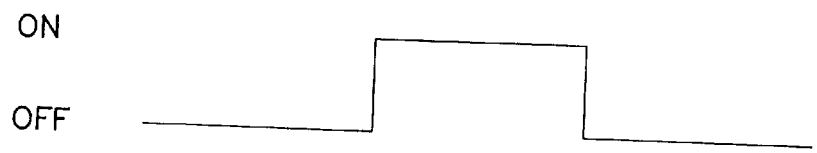

Referring now to FIG. 3, the occurrence of noise due to MIO concurrent with the applied vibration is illustrated. The top curve shows the electrogram signal, taken between 34 and 35 (as seen in FIG. 1); the bottom curve is a time coincident plot the output from driver 32. As is seen, noise appears on the electrogram, limited to the duration that the driver in "ON." This indicates that there is a region of MIO degradation somewhere in the lead, between the inner conductor 42 and the outer conductor 47. The principal component of the noise signal spectrum is at the drive frequency, which is typically around 1900 Hz for a stylet; the sensing channel can be provided with an appropriate bandpass.

Figure 4:
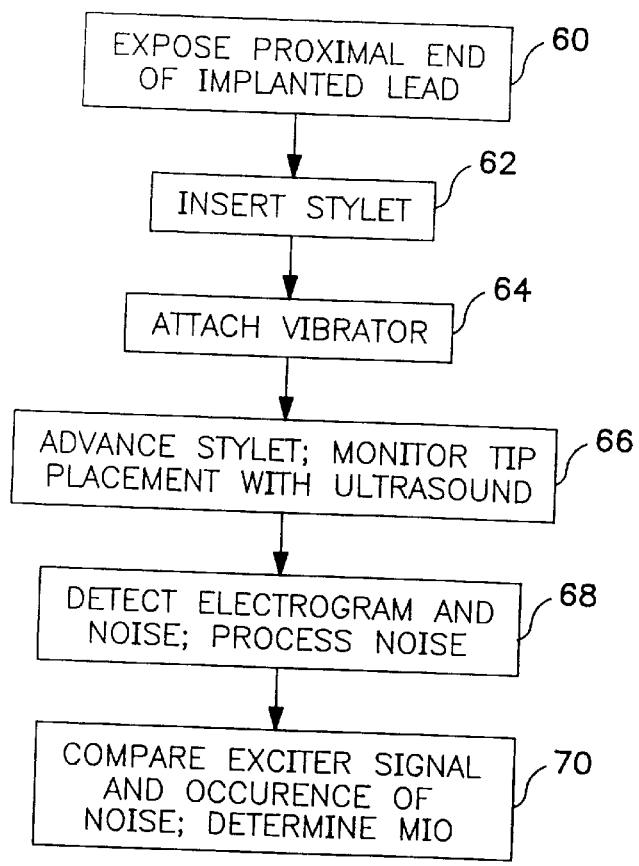
FIG. 4 is a flow diagram showing the primary steps of the method of this invention.

Referring now to FIG. 4, there are illustrated the primary steps in carrying out the MIO detection method of this invention. Initially, as shown at 60, the proximal end of the lead is exposed so that it can be connected to the driver 32 through the clamp 33. As mentioned above, the step of releasing the proximal end of the lead is done in any event at the time of a pacemaker replacement. Next, at 62, the stylet is inserted into the lead. At this time, it is desirable to insert the stylet fully until it reaches the proximal end of the lead, to ensure that the test can be carried out. After partially withdrawing the stylet, the driver and clamp are attached, as indicated at 64, and the amplitude and frequency of the driver output are adjusted. Next, at 66, the stylet is advanced, and the location of the stylet tip may be monitored by Ultrasound device 40. At 68, the electrogram is detected and processed, and any noise component may also be processed, as by filtering to find noise components that correspond to the frequency of the driver. At 70, the exciter signal is compared with the occurrence of any noise, for a determination of MIO. This comparison can be visual, by the physician handling the replacement; it may also be automatic, as by correlation of the signals by suitable hardware and/or software. While not illustrated, it is of course understood that if MIO degradation is detected, the implanted lead is replaced with a new lead, using known techniques.

It is to be noted that steps 66, 68 and 70 may be repeated, with variations. Thus, the stylet may be inserted so that the tip is advanced to different locations and the driver parameters (amplitude and frequency) adjusted, following which the detection and processing steps are repeated. Of course, if the patient requires pacing support during the procedure, temporary pacing is provided, preferably fixed rate pacing such as in a VDD mode.

For the preferred embodiment of an exciter, care must be taken to eliminate or at least minimize leakage voltage from the exciter to the stylet, which could interfere with the MIO-caused noise signal detection. This possible problem can be handled by appropriately insulating the stylet, either the entire stylet or the contact area where the exciter is attached to it. The insulation may suitably be a polyimide or other suitable sleeve, which can slide on over the proximal end of the lead like a sock.

It is to be noted that while the invention has particular applicability to detecting MIO in a bipolar lead, it may also be used for detecting MIO degradation in unipolar or multipolar leads. Also, the invention is not limited to use of the type of exciter illustrated as the preferred embodiment, and indeed is not limited to exciting or vibrating a stylet. Any form of vibration or flexing of the lead can be employed, either from an external source or from internal forces, so long as the timing of the flexing or vibration is determined and used to enable an examination of coincident noise across the lead conductors, or across the lead conductor and an indifferent electrode in the case of a unipolar lead. Any suitable motion detector or other transducer can be utilized to determine when the lead is in a state of flexion or vibration.

What is claimed is:

1. A system for detecting MIO degradation in a bipolar pacing lead, said lead having two conductors and a lumen extending substantially therethrough, comprising:

a stylet of predetermined length, at least a portion of said stylet being inserted within said lumen and a proximal portion remaining outside of said lead lumen;

vibration driving means for vibrating said lead, said vibration means further comprising connecting means for connecting to said stylet proximal portion so as to vibrate said stylet; and sensing means for sensing signals across said two conductors, whereby noise attributable to MIO degradation can be determined from said sensed signals.

2. The system as described in claim 1, wherein said vibration driving means flexes said stylet at a sonic frequency.

3. The system as described in claim 1, wherein said two conductors are coils, one of said coil conductors being positioned within the other, said lead having insulation between said two coil conductors, and wherein said vibration driving means drives said stylet so as to shake said insulation.

4. The system as described in claim 1, further comprising processing means for processing said sensed signals, and correlation means for correlating a sensed noise signal with said stylet vibration.

5. The system as described in claim 4, wherein said correlation means comprises means for comparing the timing of said sensed noise signal and said stylet vibration.

6. The system as described in claim 1, wherein said driving means drives said stylet at a sonic frequency, and further comprising ultrasound detection means for detecting the position of said stylet and thus the position of said MIO degradation.

7. A method of detecting MIO degradation in an implanted bipolar pacing lead, said lead having inner and outer conductors and a lumen therethrough, comprising:

exposing a proximal portion of said lead, said portion including the proximal tip;

inserting a stylet into said lumen, leaving at least a proximal portion of said stylet out of said lumen;

producing vibrations in said stylet which are propagated along said stylet;

obtaining signals across said inner and outer conductors while producing said stylet vibrations; and determining from said signals whether an MIO degradation exists in said lead.

8. The method as described in claim 7, comprising determining from said obtained signals whether there is a noise component that correlates with said produced vibrations.

9. The method as described in claim 8, comprising driving said proximal lead portion with an acoustic frequency driver.

10. The method as described in claim 7, comprising determining whether there is a noise component in said obtained signals.

11. The method as described in claim 10, comprising correlating the timing of said noise signals with the timing of said produce vibrations.

12. The method as described in claim 10, comprising comparing the frequency characteristics of said noise component with the frequency characteristics of said stylet vibrations.

13. The method as described in claim 7, comprising vibrating said stylet with a force applied to said stylet proximal portion, and adjusting the amplitude of said force while determining whether any noise component appears in said signals which correlates with said vibrations.

14. A system for detecting MIO degradation in an implanted pacing lead, said lead having at least one conductor, comprising:

vibration means for vibrating said lead, sensing means for sensing noise signals between a pair of electrical points, at least one of said points being said at least one conductor, timing means for determining the timing of said vibrating, and MIO means for analyzing said sensed noise signals during said vibrating and determining when noise exists which is coincidental with said timing, thereby providing an indication of MIO degradation in said lead.

15. The system as described in claim 14, wherein said lead is a bipolar lead having two conductors, and said sensing means comprises means for sensing said noise signals between said two conductors.

16. A system for detecting MIO degradation in an implanted bipolar pacing lead, said lead having a pair of conductors, comprising:

first sensing means for sensing when said lead is in a state of vibrating or flexing;

second sensing means for sensing noise signals between said conductors; and

MIO means for analyzing said sensed noise signals during said state and determining when noise exists which is coincident with said state, thereby providing an indication of MIO degradation in said lead.

* * * * *